(12) United States Patent
Sutherland et al.

(10) Patent No.: US 11,446,458 B2
(45) Date of Patent: Sep. 20, 2022

(54) APPARATUS AND METHOD FOR A LUNG ISOLATION TUBE ASSEMBLY

(71) Applicants: Caleb Sutherland, McDonald, TN (US); Mark Bryan, Goldendale, WA (US)

(72) Inventors: Caleb Sutherland, McDonald, TN (US); Mark Bryan, Goldendale, WA (US)

(73) Assignee: LIT Device LLC, Chattanooga, TN (US)

( * ) Notice: Subject to any disclaimer, the term of this patent is extended or adjusted under 35 U.S.C. 154(b) by 395 days.

(21) Appl. No.: 16/561,608

(22) Filed: Sep. 5, 2019

(65) Prior Publication Data

US 2020/0069898 A1    Mar. 5, 2020

Related U.S. Application Data

(60) Provisional application No. 62/727,336, filed on Sep. 5, 2018.

(51) Int. Cl.
*A61M 16/04* (2006.01)
*A61M 16/20* (2006.01)

(52) U.S. Cl.
CPC .... *A61M 16/0404* (2014.02); *A61M 16/0434* (2013.01); *A61M 16/0486* (2014.02); *A61M 16/201* (2014.02); *A61M 2210/1039* (2013.01)

(58) Field of Classification Search
CPC .............. A61M 16/04; A61M 16/0402; A61M 16/0404; A61M 16/0409; A61M 16/0434; A61M 16/0459; A61M 16/0465; A61M 16/0486; A61M 16/20; A61M 16/201; A61M 16/206; A61M 16/0833; A61M 2210/1039; A61M 29/223
See application file for complete search history.

(56) References Cited

U.S. PATENT DOCUMENTS

| | | | | |
|---|---|---|---|---|
| 2,791,217 A | * | 5/1957 | Iskander | A61M 16/0404 128/205.24 |
| 4,489,721 A | * | 12/1984 | Ozaki | A61M 16/0463 128/205.24 |
| 4,593,717 A | | 6/1986 | Levasseur | |
| 4,674,496 A | * | 6/1987 | Svadjian | A61M 16/20 128/205.24 |

(Continued)

FOREIGN PATENT DOCUMENTS

| | | | | |
|---|---|---|---|---|
| WO | WO-9919013 A1 | * | 4/1999 | ........ A61M 16/0486 |
| WO | WO-2007141487 A1 | * | 12/2007 | ............ A61M 16/20 |

*Primary Examiner* — Colin W Stuart
(74) *Attorney, Agent, or Firm* — Miller & Martin PLLC

(57) ABSTRACT

A lung isolation tube assembly including a control valve that is adapted to be moved between a left lumen position, a right lumen position, and a both lumens position, a connector that is in fluid communication with the control valve, and a tube that is in fluid communication with the connector. The tube includes a left lumen that is in fluid communication with the connector and a right lumen that is in fluid communication with the connector. The assembly also includes a first cuff that is disposed around a portion of the right lumen and the left lumen and a second cuff that is disposed around the left lumen. The assembly is adapted to convey airflow or oxygen to a human lung via at least one of the left lumen and the right lumen. A method for isolating a human lung.

16 Claims, 18 Drawing Sheets

(56) References Cited

U.S. PATENT DOCUMENTS

| | | | |
|---|---|---|---|
| 5,207,641 A * | 5/1993 | Allton | A61M 16/0463 |
| | | | 137/625.22 |
| 5,392,772 A | 2/1995 | Zilbershtein | |
| 5,746,199 A * | 5/1998 | Bayron | A61M 16/0463 |
| | | | 128/205.24 |
| 6,609,521 B1 * | 8/2003 | Belani | A61M 16/04 |
| | | | 128/207.14 |
| 6,953,450 B2 | 10/2005 | Baldwin et al. | |
| 7,478,636 B2 | 1/2009 | Masden et al. | |
| 7,581,541 B2 | 9/2009 | Madsen et al. | |
| 9,730,661 B2 | 8/2017 | Li et al. | |
| 10,016,575 B2 | 7/2018 | Vazales et al. | |
| 10,137,293 B2 | 11/2018 | Hamidian Jahromi et al. | |
| 10,143,580 B2 | 12/2018 | Batterson et al. | |
| 10,279,161 B2 | 5/2019 | Ziv et al. | |
| 2012/0017914 A1 * | 1/2012 | Watt Lanyau | A61M 16/0486 |
| | | | 128/207.14 |
| 2015/0217070 A1 * | 8/2015 | Song | A61M 16/0833 |
| | | | 128/202.27 |
| 2016/0228129 A1 | 8/2016 | Levy | |
| 2017/0072154 A1 * | 3/2017 | Hoftman | A61M 16/0486 |
| 2017/0258991 A1 | 9/2017 | Tornblom | |
| 2019/0022370 A1 | 1/2019 | Zushi et al. | |
| 2019/0125232 A1 | 5/2019 | Wine et al. | |

* cited by examiner

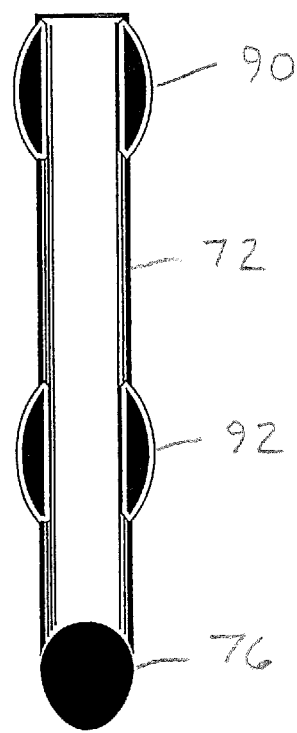
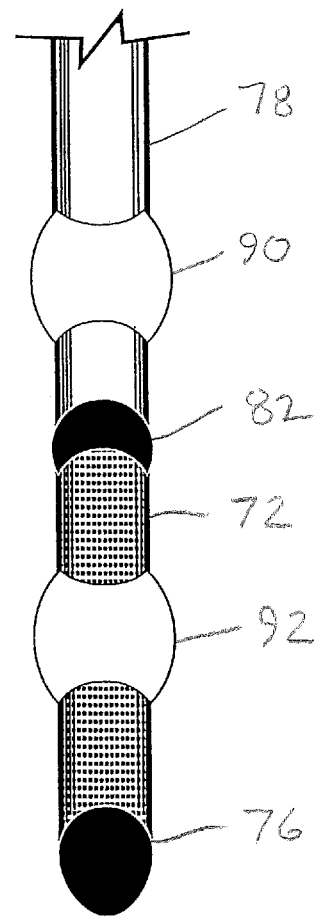
FIGURE 6     FIGURE 7

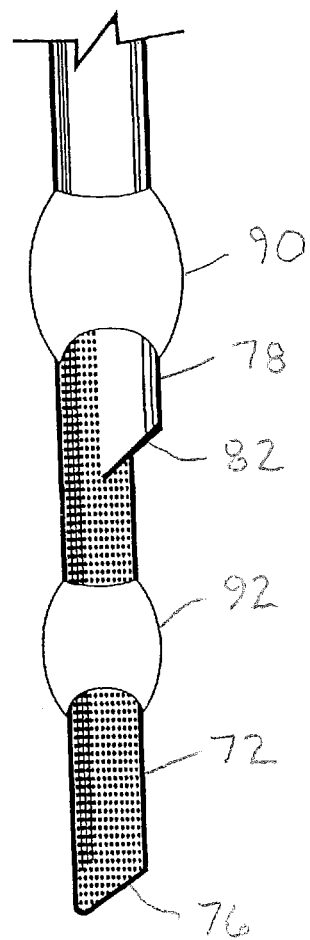 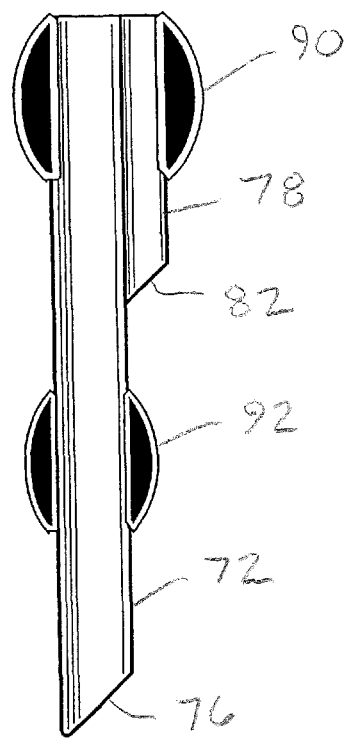
FIGURE 8
FIGURE 9

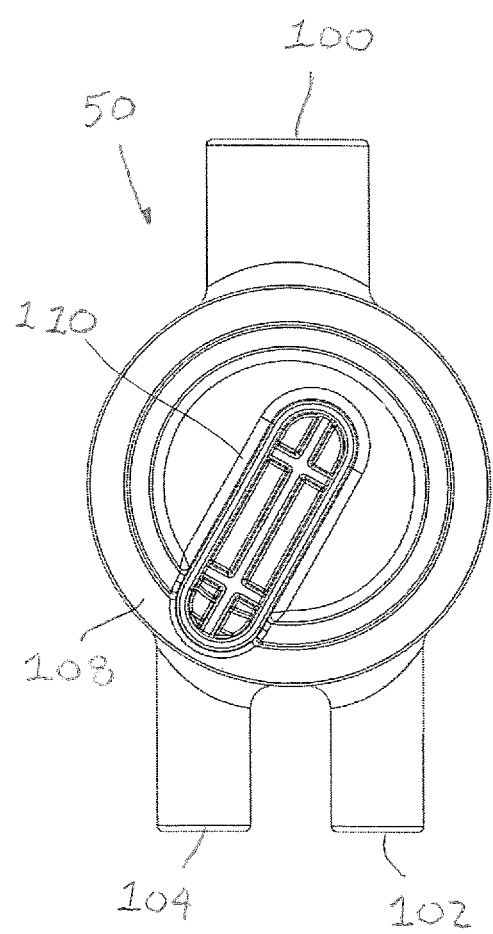 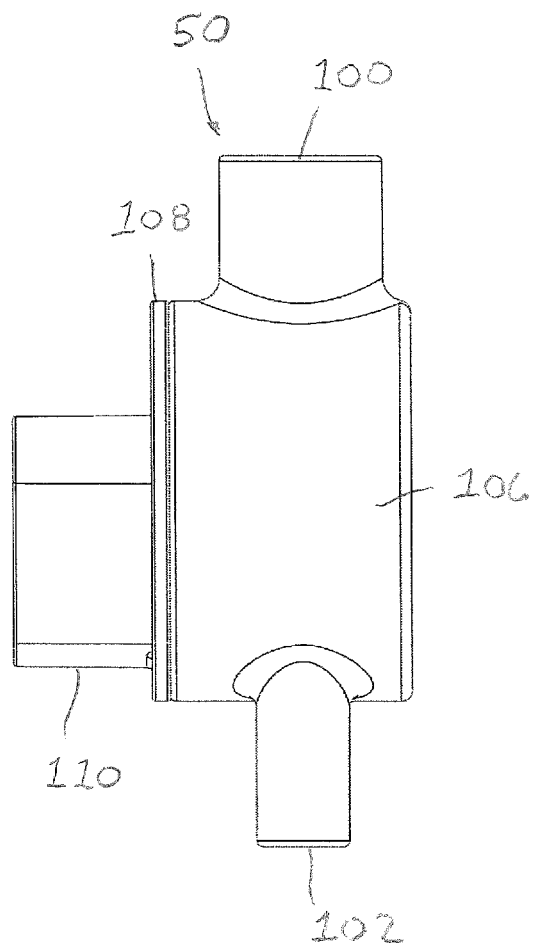
FIGURE 13  FIGURE 14

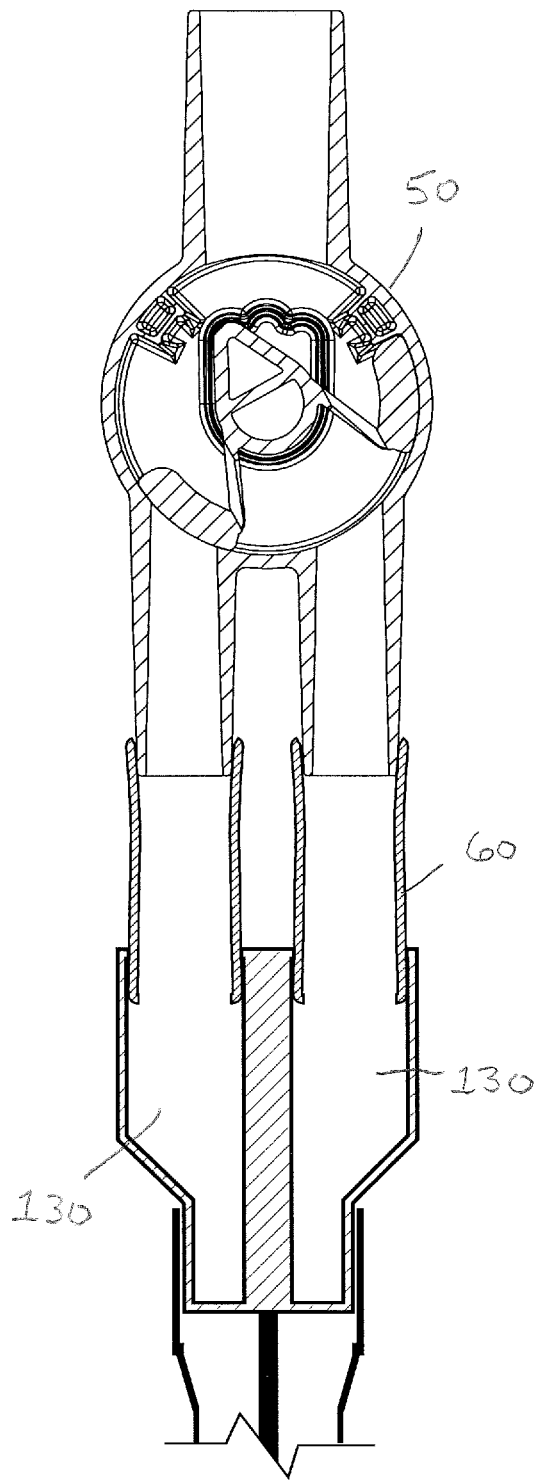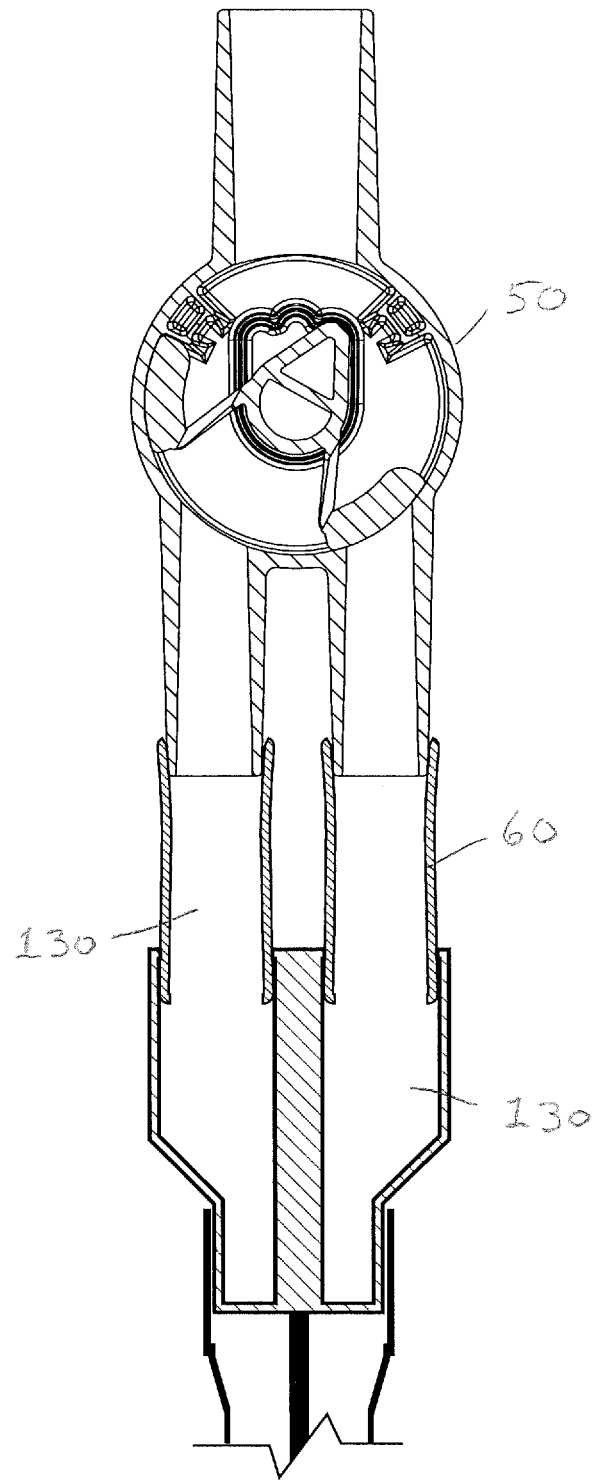
FIGURE 22     FIGURE 23

APPARATUS AND METHOD FOR A LUNG ISOLATION TUBE ASSEMBLY

CROSS-REFERENCES TO RELATED APPLICATIONS/PATENTS

This application relates back to and claims the benefit of priority from U.S. Provisional Application for Patent Ser. No. 62/727,336 titled "Lung Isolation Tube" and filed on Sep. 5, 2018.

FIELD OF THE INVENTION

The present invention relates generally to apparatuses and methods for isolating a human lung, and particularly to apparatuses and methods for a lung isolation tube (LIT) assembly.

BACKGROUND AND DESCRIPTION OF THE PRIOR ART

It is known to use apparatuses and methods to isolate a human lung using a lung isolation tube. Conventional apparatuses and methods, however, suffer from one or more disadvantages. For example, conventional lung isolation tubes and methods require a connector set with clamps in order to close airflow through a lumen. Conventional lung isolation tubes and methods also employ undesirably complex lumen control valves. Further, conventional lung isolation tubes and methods include complex lumen suction ports. Still further, conventional lung isolation tubes and methods are difficult to utilize in emergency situations in the field.

It would be desirable, therefore, if an apparatus and method for a lung isolation tube assembly could be provided that would not require a connector set with clamps in order to close airflow through a lumen. It would also be desirable if such an apparatus and method for a lung isolation tube assembly could be provided that would not require complex lumen control valves. It would be further desirable if such an apparatus and method for a lung isolation tube assembly could be provided that would not include complex lumen suction ports. It would be still further desirable if such an apparatus and method for a lung isolation tube assembly could be provided that would be easy to use in emergency situations in the field.

ADVANTAGES OF THE PREFERRED EMBODIMENTS OF THE INVENTION

Accordingly, it is an advantage of the preferred embodiments of the invention claimed herein to provide an apparatus and method for a lung isolation tube assembly that uses a control valve in order to close airflow through the lumens. It is also an advantage of the preferred embodiments of the invention claimed herein to provide an apparatus and method for a lung isolation tube assembly that does not require complex lumen control valves. It is another advantage of the preferred embodiments of the invention claimed herein to provide an apparatus and method for a lung isolation tube assembly that does not include a complex lumen suction port. It is yet another advantage of the preferred embodiments of the invention claimed herein to provide an apparatus and method for a lung isolation tube assembly that is easy to use in emergency situations in the field.

Additional advantages of the preferred embodiments of the invention will become apparent from an examination of the drawings and the ensuing description.

EXPLANATION OF THE TECHNICAL TERMS

The use of the terms "a," "an," "the," and similar terms in the context of describing the invention are to be construed to cover both the singular and the plural, unless otherwise indicated herein or clearly contradicted by context. The terms "comprising" "having," "including," and "containing" are to be construed as open-ended terms (i.e., meaning "including, but not limited to,") unless otherwise noted. The terms "substantially," "generally," and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic. All methods described herein can be performed in any suitable order unless otherwise specified herein or clearly indicated by context.

Terms concerning attachments, coupling and the like, such as "attached," "connected," and "interconnected," refer to a relationship wherein structures are secured or attached to one another either directly or indirectly through intervening structures, as well as both moveable and rigid attachments or relationships, unless specified herein or clearly indicated by context. The term "operatively connected" is such an attachment, coupling or connection that allows the pertinent structures to operate as intended by virtue of that relationship.

The use of any and all examples or exemplary language (e.g., "such as," "preferred," and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity. Several terms are specifically defined herein. These terms are to be given their broadest reasonable construction consistent with such definitions, as follows:

As used herein, the term "lumen" means a cavity or channel within a tubular structure.

As used herein, the term "tube" means a long (relative to its width), substantially hollow tubular structure having a substantially circular, round, or ovate cross-section.

SUMMARY OF THE INVENTION

The apparatus of the invention comprises a lung isolation tube assembly. The preferred lung isolation tube assembly comprises a control valve that is adapted to be moved between a left lumen position, a right lumen position, and a both lumens position, a connector that is in fluid communication with the control valve, and a tube that is in fluid communication with the connector. The preferred tube comprises a left lumen that is in fluid communication with the connector and has a left lumen proximate end opening and a left lumen distal end opening and a right lumen that is in fluid communication with the connector and has a right lumen proximate end opening and a right lumen distal end opening. The preferred lung isolation tube assembly also comprises a first cuff that is disposed around a portion of the right lumen and a portion of the left lumen and a second cuff that is disposed around a portion of the left lumen. The preferred lung isolation tube assembly is adapted to convey airflow or oxygen to a human lung via at least one of the left lumen and the right lumen.

The method of the invention comprises a method for isolating a human lung. The preferred method comprises providing a lung isolation tube assembly. The preferred lung isolation tube assembly comprises a control valve that is adapted to be moved between a left lumen position, a right lumen position, and a both lumens position, a connector that is in fluid communication with the control valve, and a tube that is in fluid communication with the connector. The preferred tube comprises a left lumen that is in fluid communication with the connector and has a left lumen proximate end opening and a left lumen distal end opening and a right lumen that is in fluid communication with the connector and has a right lumen proximate end opening and a right lumen distal end opening. The preferred lung isolation tube assembly also comprises a first cuff that is disposed around a portion of the right lumen and a portion of the left lumen and a second cuff that is disposed around a portion of the left lumen. The preferred lung isolation tube assembly is adapted to convey airflow or oxygen to a human lung via at least one of the left lumen and the right lumen. The preferred method also comprises inserting the tube into a human and supplying airflow or oxygen to the lung isolation tube assembly.

BRIEF DESCRIPTION OF THE DRAWINGS

The presently preferred embodiments of the invention are illustrated in the accompanying drawings, in which like reference numerals represent like parts throughout, and in which:

FIG. 6 is a top view of the preferred distal end of the tube illustrated in FIGS. 1-5.

FIG. 7 is a partial sectional top view of the preferred distal end of the tube illustrated in FIGS. 1-6.

FIG. 8 is a side view of the preferred distal end of the tube illustrated in FIGS. 1-7.

FIG. 9 is a partial sectional side view of the preferred distal end of the tube illustrated in FIGS. 1-8.

FIG. 13 is a top view of the preferred valve illustrated in FIGS. 1-5 and 11-12.

FIG. 14 is a side view of the preferred valve illustrated in FIGS. 1-5 and 11-13.

FIG. 22 is a partial sectional view of the preferred connector illustrated in FIGS. 1-5.

FIG. 23 is a partial sectional view of the preferred connector illustrated in FIGS. 1-5.

DESCRIPTION OF THE PREFERRED EMBODIMENTS OF THE INVENTION

Figure 1:
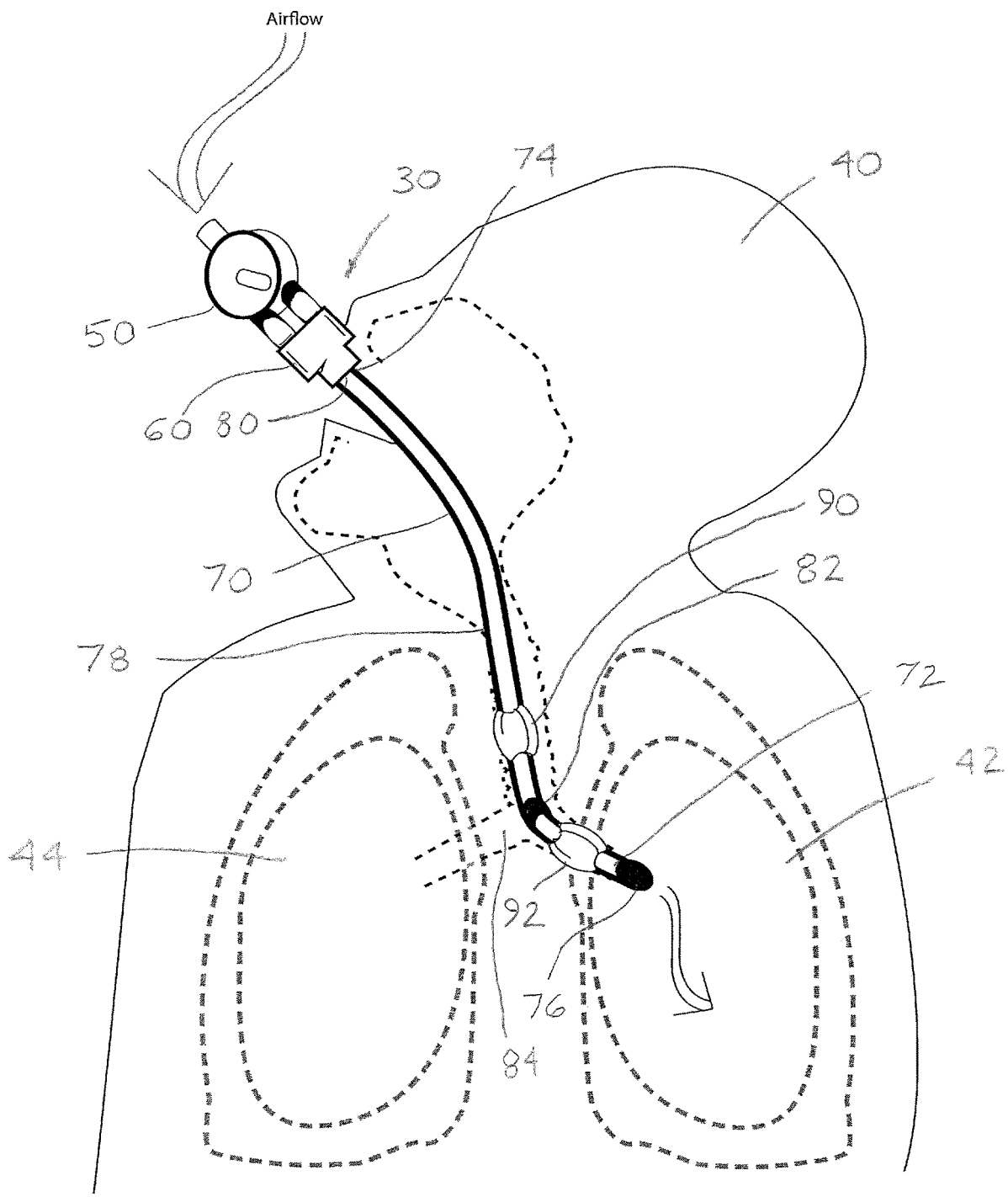
FIG. 1 is a perspective view of the preferred embodiment of the lung isolation tube assembly in accordance with the present invention shown inserted into an exemplary human in the left lumen position.

Referring now to the drawings, the preferred embodiment of the lung isolation tube assembly in accordance with the present invention is illustrated by FIGS. 1 through 23. As shown in FIGS. 1-23, the preferred lung isolation tube assembly is adapted to use a control valve in order to close airflow or oxygen flow through the lumens. The preferred embodiment of the lung isolation tube assembly does not require complex lumen control valves. The preferred embodiment of the lung isolation tube assembly does not include a complex lumen suction port. The preferred embodiment of the lung isolation tube assembly is easy to use in emergency situations in the field.

Referring now to FIG. 1, a perspective view of the preferred embodiment of the lung isolation tube assembly in accordance with the present invention shown inserted into an exemplary human in the left lumen position is illustrated. As shown in FIG. 1, the preferred lung isolation tube assembly is designated generally by reference numeral 30 and exemplary human is designated generally by reference numeral 40. Exemplary human 40 has left lung 42 and right lung 44. Preferred lung isolation tube assembly 30 comprises a control valve such as switch valve 50 which is adapted to be moved between a left lumen position, a right lumen position, and a both lumens position. More particularly, in the left lumen position, preferred switch valve 50 directs airflow or oxygen to left lung 42 of exemplary human 40. In the right lumen position, preferred switch valve 50 directs airflow or oxygen to right lung 44 of exemplary human 40. In the both lumens position, preferred switch valve 50 directs airflow or oxygen to left lung 42 and right lung 44 of exemplary human 40.

Still referring to FIG. 1, preferred lung isolation tube assembly 30 also comprises connector 60 which is in fluid communication with preferred switch valve 50. Preferred lung isolation tube assembly 30 further comprises tube 70 which is in fluid communication with preferred connector 60. Preferred tube 70 comprises left lumen 72 (see also FIGS. 5-10) which is in fluid communication with connector 60 and has left lumen proximate end opening 74 and left lumen distal end opening 76. Preferred tube 70 also comprises right lumen 78 (see also FIGS. 5-10) which is in fluid communication with connector 60 and has right lumen proximate end opening 80 and right lumen distal end opening 82. Preferably, the left lumen distal end extends beyond the right lumen distal end and into a human left lung. Preferred right lumen distal end is adapted to extend to human right bronchus 84.

Still referring to FIG. 1, preferred lung isolation tube assembly 30 still further comprises first cuff 90 which is disposed around a portion of right lumen 78 and a portion of left lumen 72. Preferably, first cuff 90 is disposed on right lumen 78 and left lumen 72 such that it is positioned in a human trachea when the left lumen distal end is positioned in human left lung 42 and the right lumen distal end is positioned adjacent to human right bronchus 84. Preferred lung isolation tube assembly 30 also comprises second cuff 92 which is disposed around a portion of left lumen 72. Preferably, second cuff 92 is disposed around left lumen 72 such that it is positioned in a human left bronchus when the left lumen distal end is positioned in human left lung 42 and the right lumen distal end is positioned adjacent to human right bronchus 84. Preferred lung isolation tube assembly 30 is adapted to convey airflow or oxygen to a human lung via at least one of the left lumen and the right lumen. In a preferred embodiment of lung isolation tube assembly 30, an airflow or oxygen source is provided such that it is in fluid communication with control valve 50.

Figure 2:
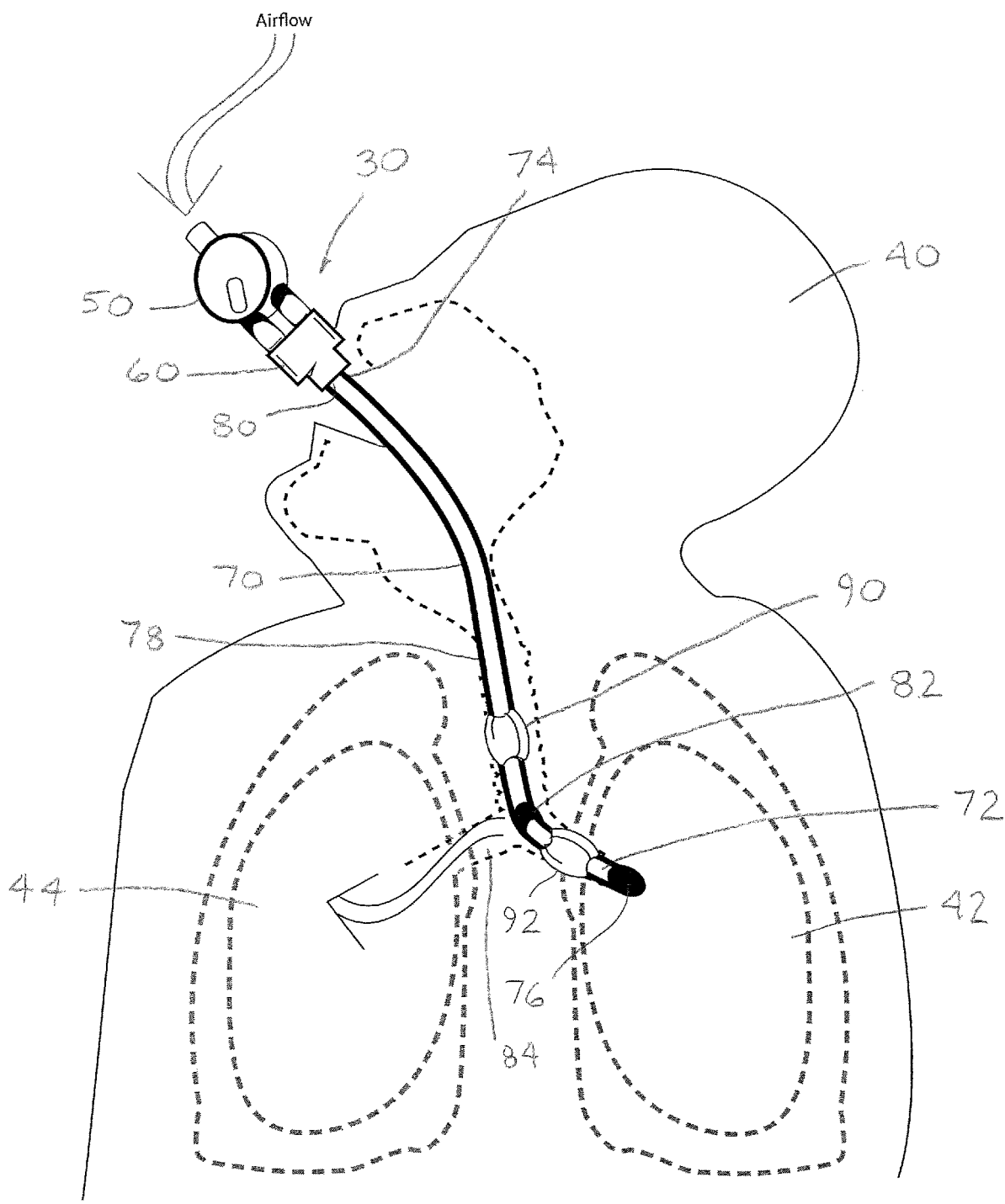
FIG. 2 is a perspective view of the preferred embodiment of the lung isolation tube assembly illustrated in FIG. 1 shown inserted into an exemplary human in the right lumen position.

Referring now to FIG. 2, a perspective view of the preferred embodiment of lung isolation tube assembly 30 is illustrated in the right lumen position. In the right lumen position, lung isolation tube assembly 30 is adapted to convey airflow or oxygen to right lung 44 of exemplary human 40.

Figure 3:
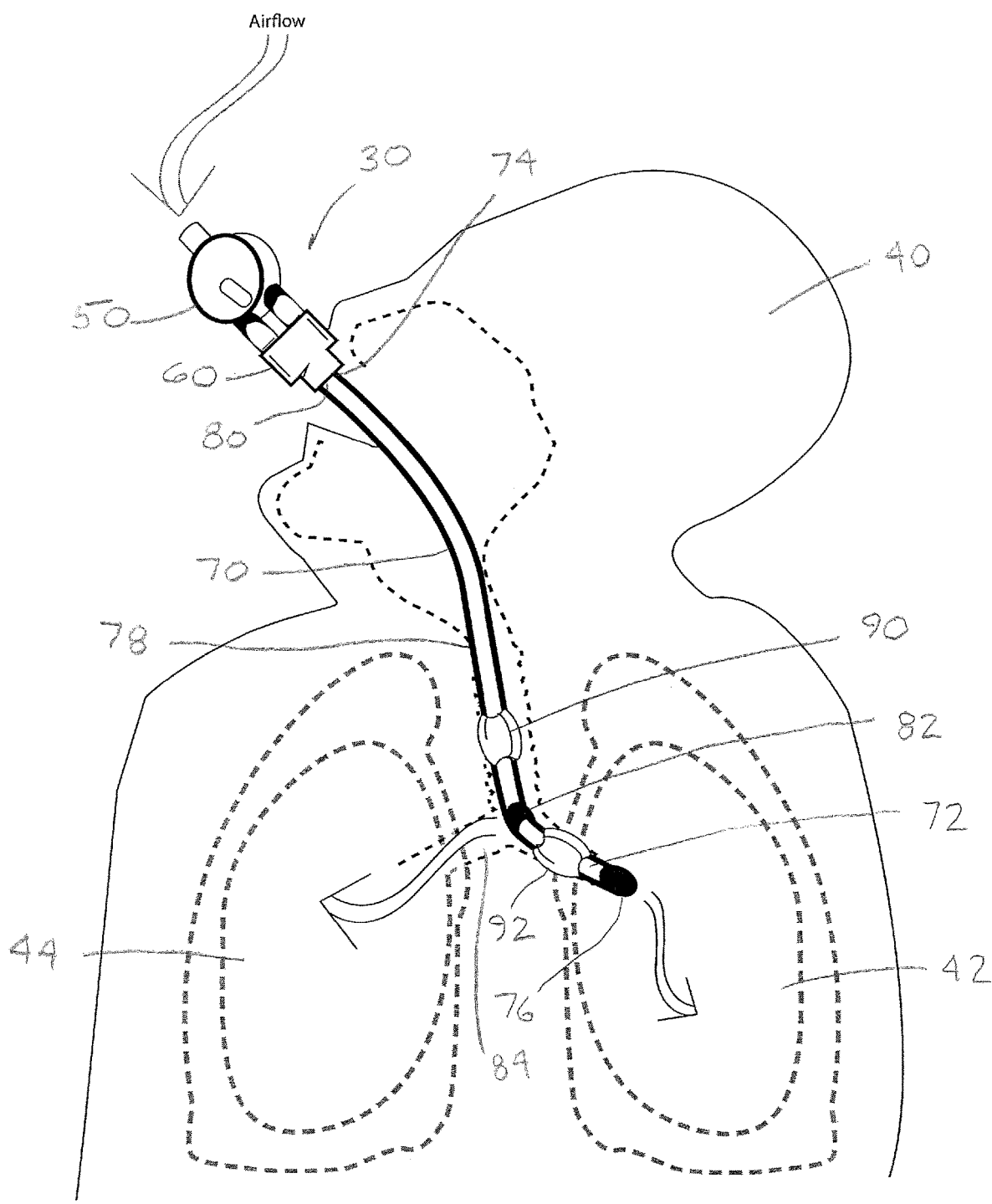
FIG. 3 is a perspective view of the preferred embodiment of the lung isolation tube assembly illustrated in FIGS. 1-2 shown inserted into an exemplary human in the both lumens position.

Referring now to FIG. 3, a perspective view of the preferred embodiment of lung isolation tube assembly 30 is illustrated in the both lumens position. In the both lumens position, the lung isolation tube assembly 30 is adapted to convey airflow or oxygen to both left lung 42 and right lung 44 of exemplary human 40.

Figure 4:
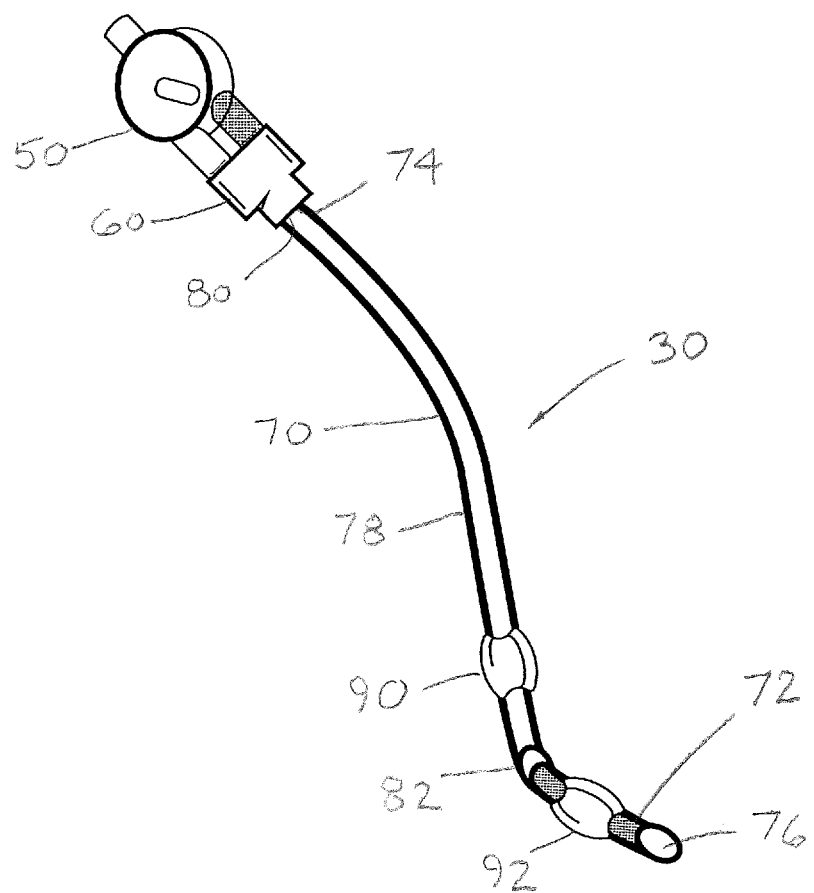
FIG. 4 is an isolated perspective view of the preferred embodiment of the lung isolation tube assembly illustrated in FIGS. 1-3 shown in the left lumen position.

Referring now to FIG. 4, an isolated perspective view of the preferred embodiment of lung isolation tube assembly 30 is illustrated in the left lumen position.

Figure 5:
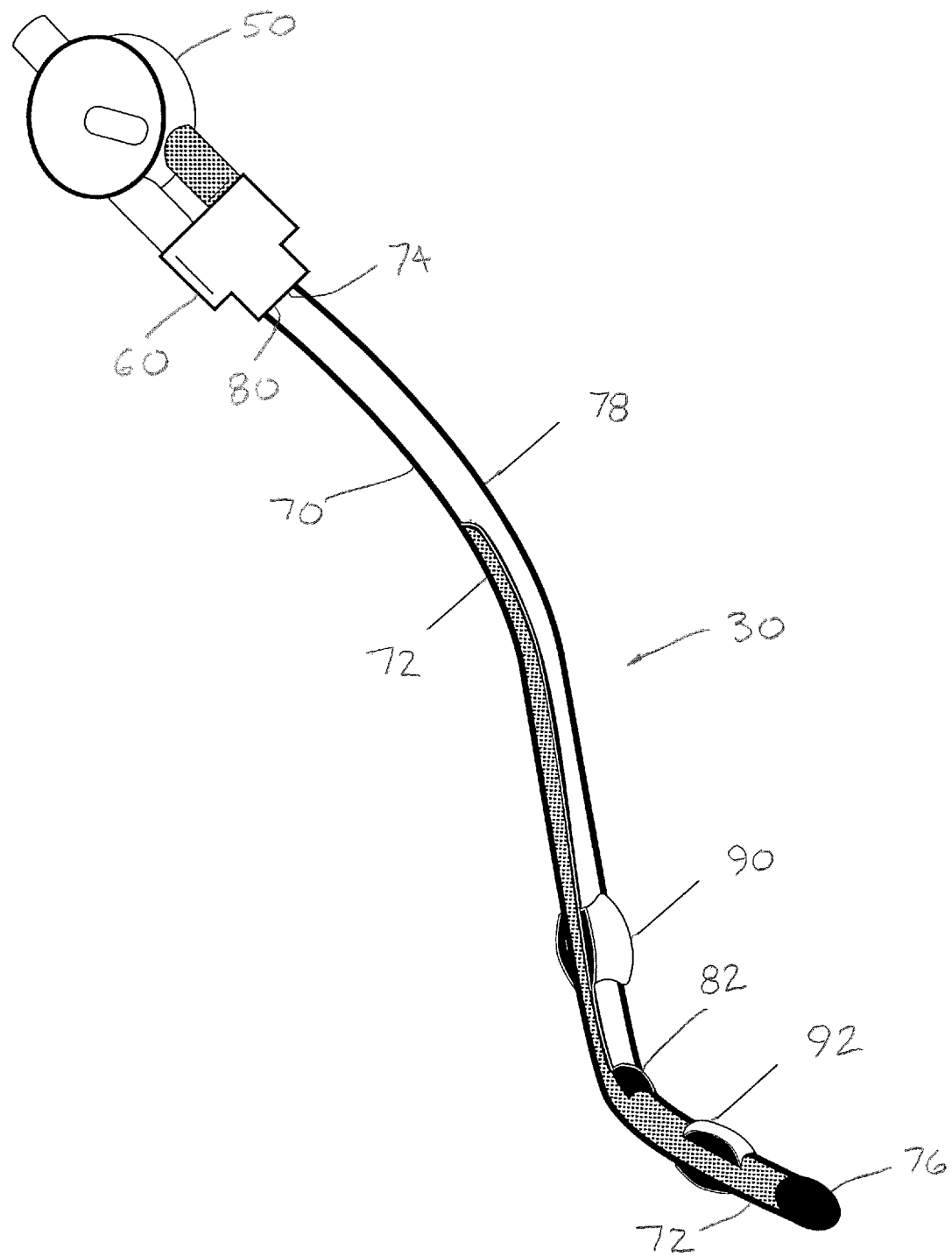
FIG. 5 is an isolated perspective view of the preferred embodiment of the lung isolation tube assembly illustrated in FIGS. 1-4 shown in the left lumen position.

Referring now to FIG. 5, an isolated perspective view of the preferred embodiment of lung isolation tube assembly 30 is illustrated in the left lumen position. As shown in FIG. 5, left lumen 72 is partially surrounded by right lumen 78.

Referring now to FIG. 6, a top view of the preferred distal end of tube 70 is illustrated.

Referring now to FIG. 7, a partial sectional top view of the preferred distal end of tube 70 is illustrated.

Referring now to FIG. 8, a side view of the preferred distal end of tube 70 is illustrated.

Referring now to FIG. 9, a partial sectional side view of the preferred distal end of tube 70 is illustrated in Figures.

Figure 10:
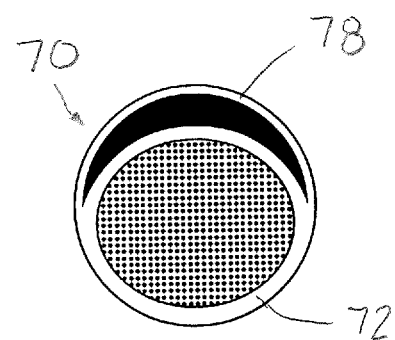
FIG. 10 is a cross-sectional view of the preferred tube illustrated in FIGS. 1-9.

Referring now to FIG. 10, a cross-sectional view of preferred tube 70 is illustrated.

Figure 11:
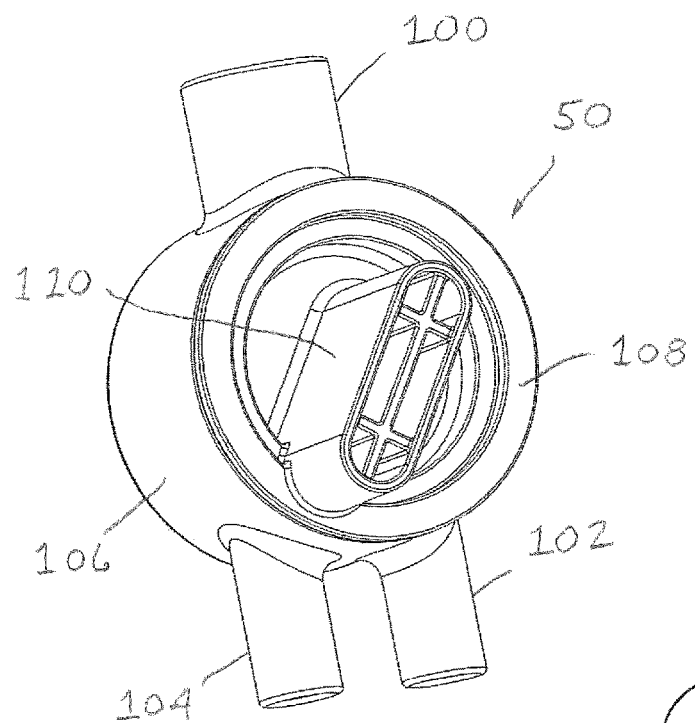
FIG. 11 is a top perspective view of the preferred valve illustrated in FIGS. 1-5.

Referring now to FIG. 11, a top perspective view of preferred valve 50 is illustrated. As shown in FIG. 11, preferred valve 50 comprises airflow inlet 100, left lumen outlet 102, right lumen outlet 104, barrel 106, rotor 108, and handle 110.

Figure 12:
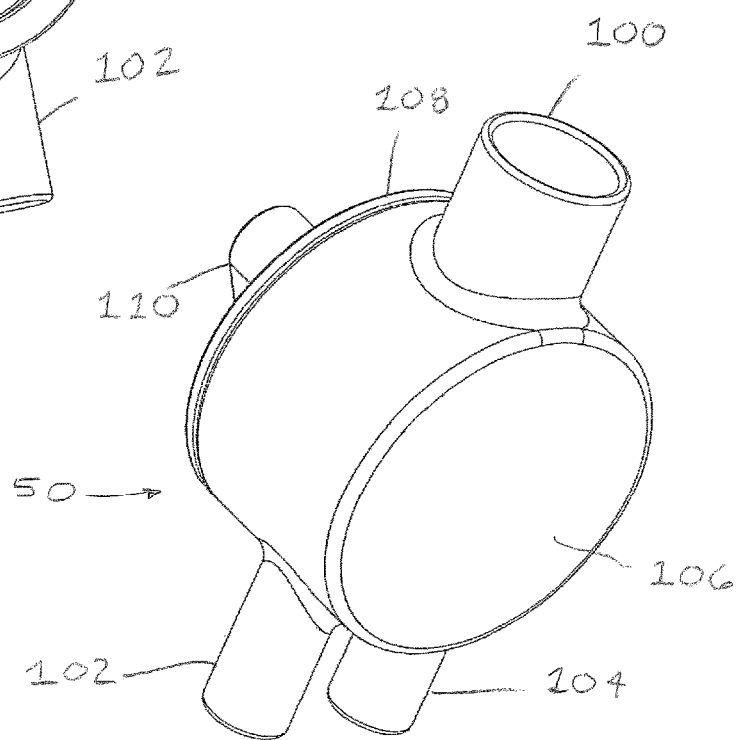
FIG. 12 is bottom perspective view of the preferred valve illustrated in FIGS. 1-5 and 11.

Referring now to FIG. 12, a bottom perspective view of preferred valve 50 is illustrated.

Referring now to FIG. 13, a top view of preferred valve 50 is illustrated.

Referring now to FIG. 14, a side view of preferred valve 50 is illustrated.

Figure 15:
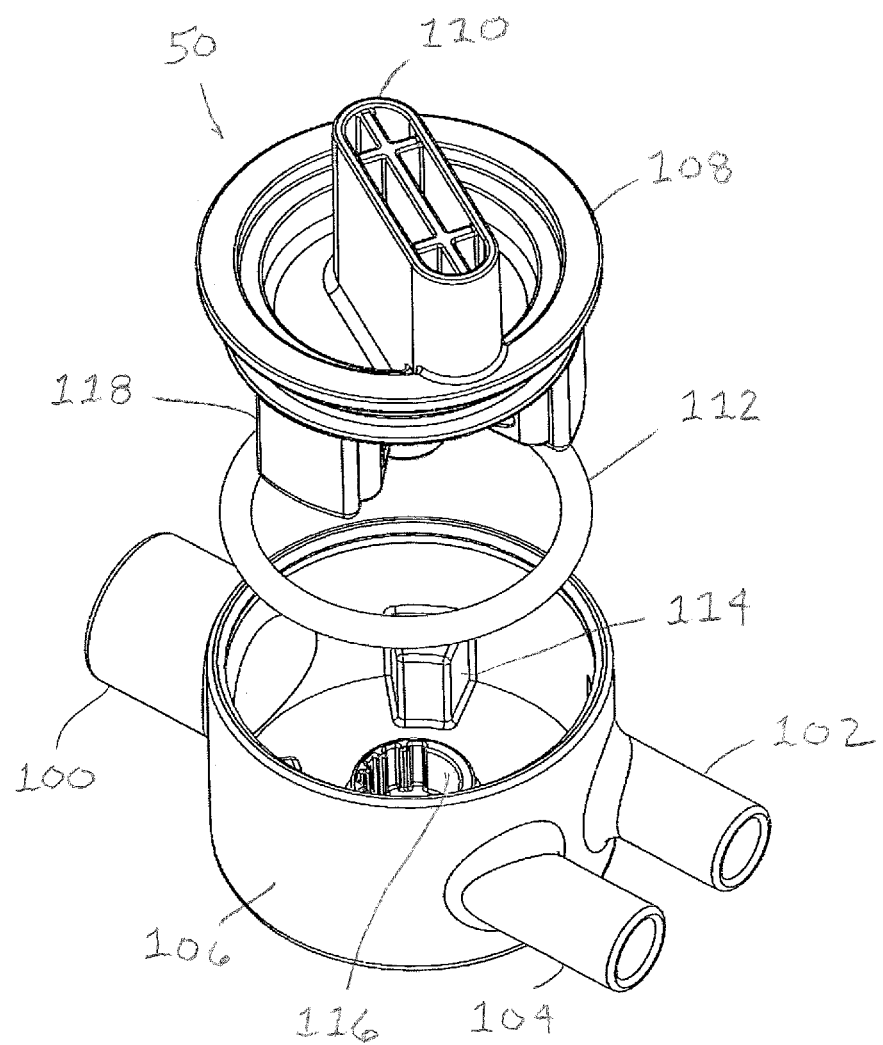
FIG. 15 is an exploded top perspective view of the preferred valve illustrated in FIGS. 1-5 and 11-14.

Referring now to FIG. 15, an exploded top perspective view of preferred valve 50 is illustrated. As shown in FIG. 15, preferred valve 50 further comprises O-ring 112. In addition, preferred barrel 106 comprises stop 114 and detent 116. Preferred rotor 108 also comprises blocker 118.

Figure 16:
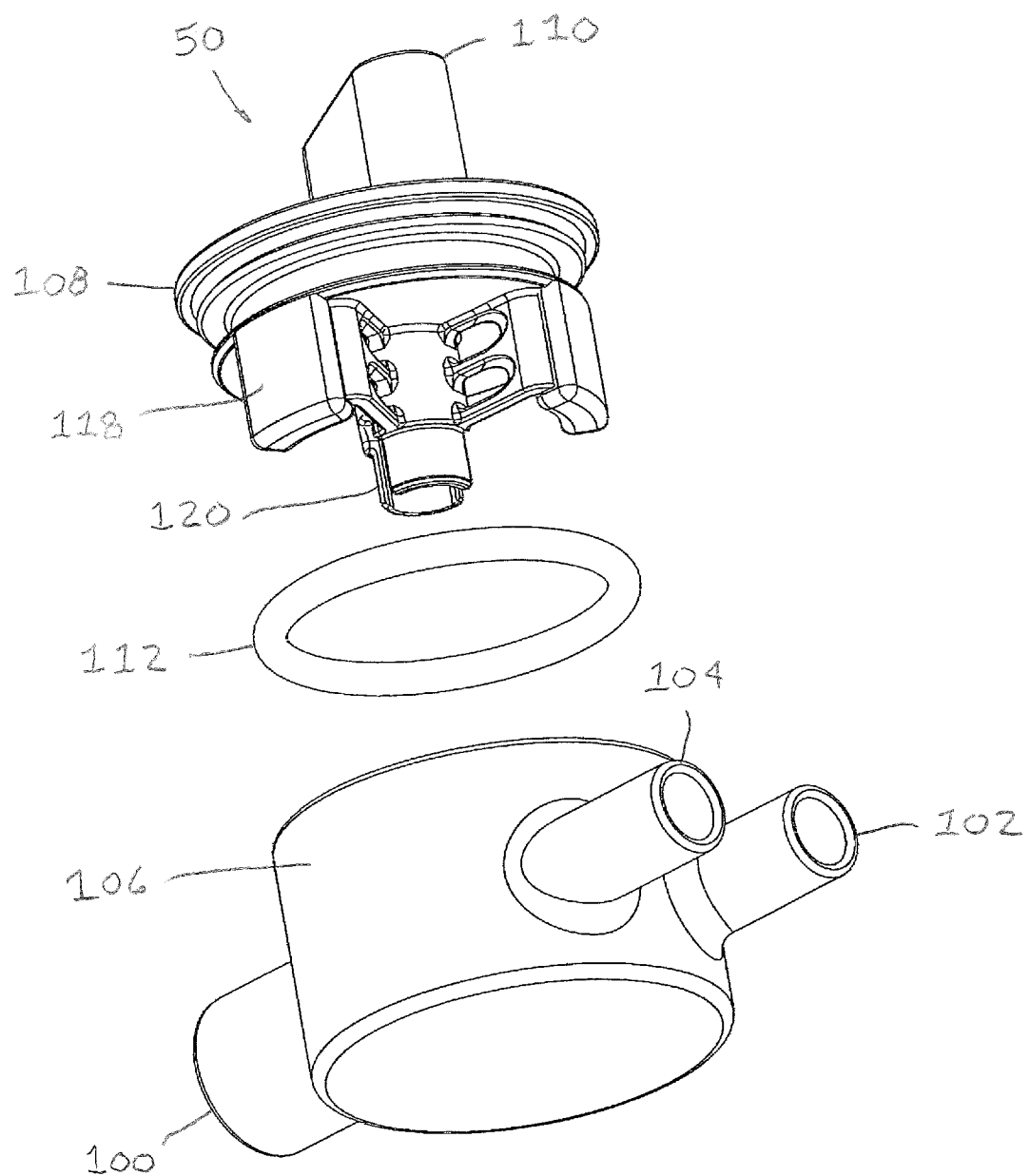
FIG. 16 is an exploded bottom perspective view of the preferred valve illustrated in FIGS. 1-5 and 11-15.

Referring now to FIG. 16, an exploded bottom perspective view of preferred valve 50 is illustrated. As shown in FIG. 16, preferred rotor 108 also comprises rotor detent 120.

Figure 17:
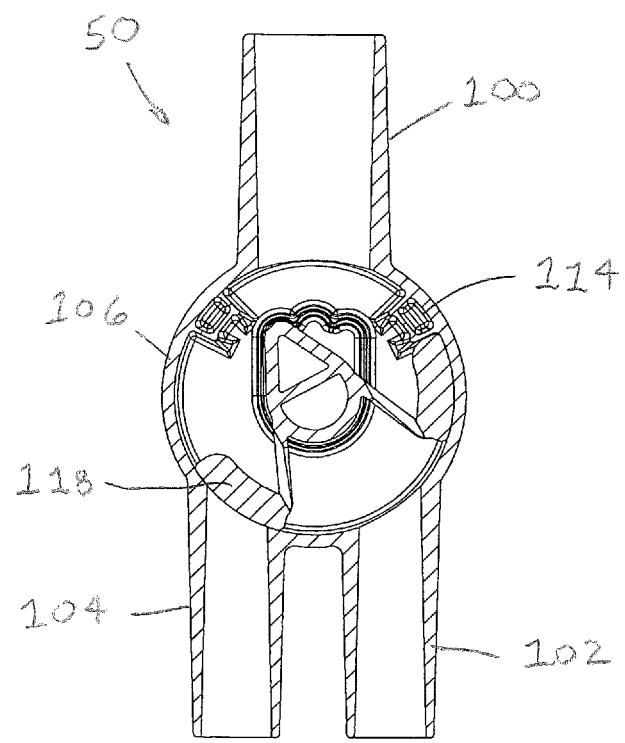
FIG. 17 is a sectional top view of the preferred valve illustrated in FIGS. 1-5 and 11-16 shown in the left lumen position.

Referring now to FIG. 17, a sectional top view of preferred valve 50 is illustrated in the left lumen position.

Figure 18:
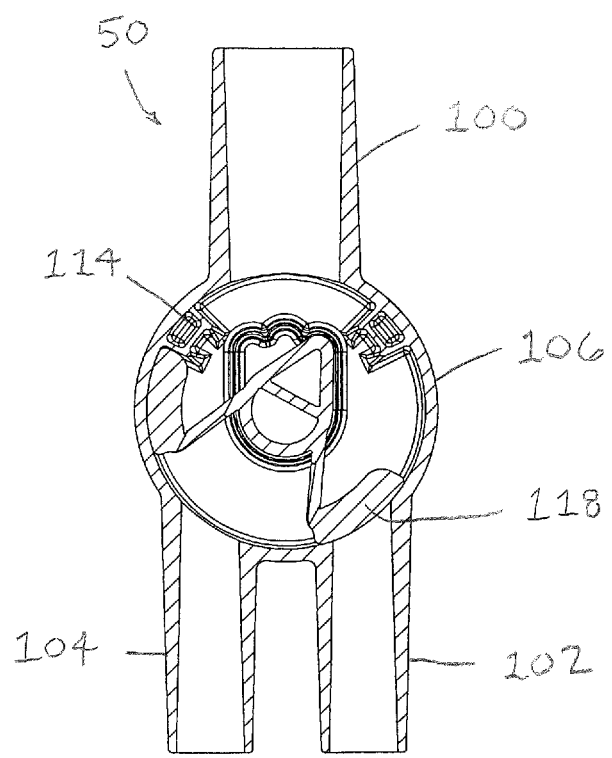
FIG. 18 is a sectional top view of the preferred valve illustrated in FIGS. 1-5 and 11-17 shown in the right lumen position.

Referring now to FIG. 18, a sectional top view of preferred valve 50 is illustrated in the right lumen position.

Figure 19:
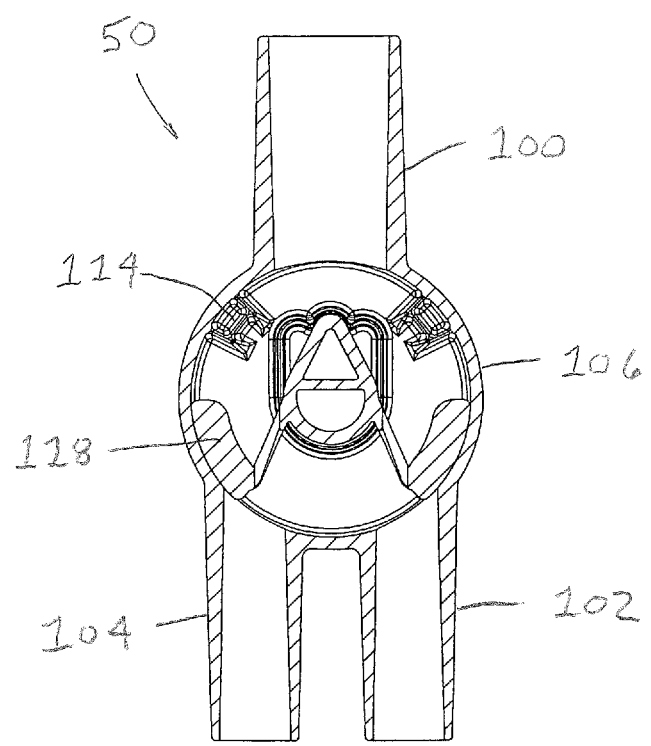
FIG. 19 is a sectional top view of the preferred valve illustrated in FIGS. 1-5 and 11-18 shown in the both lumens position.

Referring now to FIG. 19, a sectional top view of preferred valve 50 is illustrated in the both lumens position.

Figure 20:
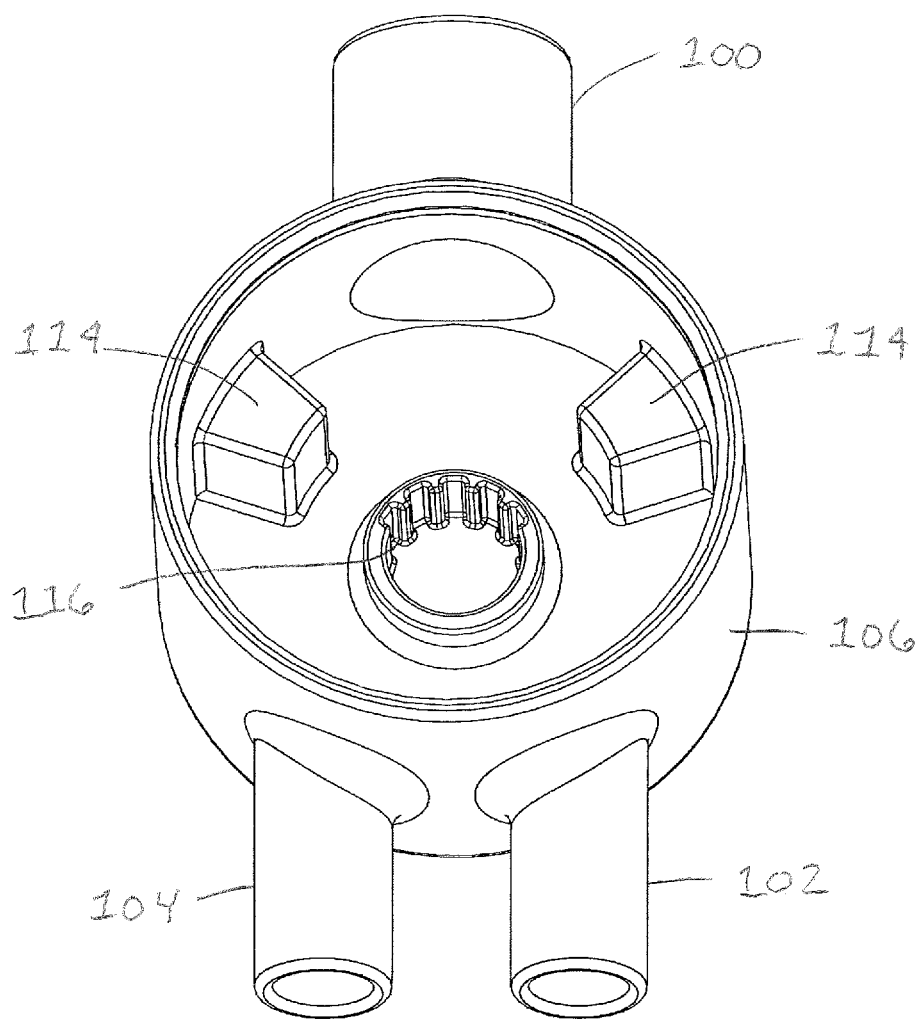
FIG. 20 is a top perspective view of the preferred barrel illustrated in FIGS. 1-5 and 11-19.

Referring now to FIG. 20, a top perspective view of preferred barrel 106 is illustrated.

Figure 21:
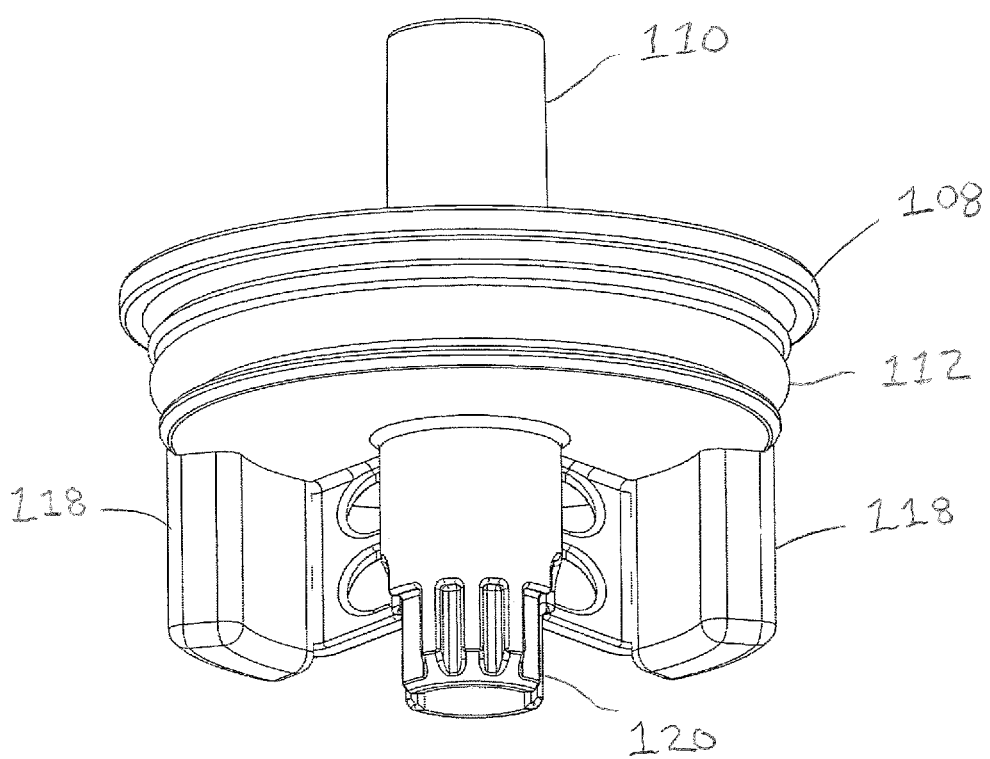
FIG. 21 is a bottom perspective view of the preferred rotor illustrated in FIGS. 1-5 and 11-20.

Referring now to FIG. 21, a bottom perspective view of preferred rotor 108 is illustrated.

Referring now to FIG. 22, a partial sectional view of preferred connector 60 is illustrated with valve 50 in the left lumen position. As shown in FIG. 22, preferred connector comprises a pair of channels 130.

Referring now to FIG. 23, a partial sectional view of preferred connector 60 is illustrated with valve 50 in the right lumen position.

The invention also comprises a method for isolating a human lung. The preferred method comprises providing a lung isolation tube assembly. The preferred lung isolation tube assembly comprises a control valve that is adapted to be moved between a left lumen position, a right lumen position, and a both lumens position, a connector that is in fluid communication with the control valve, and a tube that is in fluid communication with the connector. The preferred tube comprises a left lumen that is in fluid communication with the connector and has a left lumen proximate end opening and a left lumen distal end opening and a right lumen that is in fluid communication with the connector and has a right lumen proximate end opening and a right lumen distal end opening. The preferred lung isolation tube assembly also comprises a first cuff that is disposed around a portion of the right lumen and a portion of the left lumen and a second cuff that is disposed around a portion of the left lumen. The preferred lung isolation tube assembly is adapted to convey airflow or oxygen to a human lung via at least one of the left lumen and the right lumen. The preferred method also comprises inserting the tube into a human and supplying airflow or oxygen to the lung isolation tube assembly.

In operation, several advantages of the preferred embodiments of the lung isolation tube assembly are achieved. For example, the preferred embodiments of the lung isolation tube assembly use a control valve in order to close airflow or oxygen flow through the lumens. The preferred embodiments of the lung isolation tube assembly do not require complex lumen control valves. The preferred embodiments of the lung isolation tube assembly do not include a complex lumen suction port. The preferred embodiments of the lung isolation tube assembly are easy to use in emergency situations in the field.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A lung isolation tube assembly comprising:
   (a) a control valve, said control valve being adapted to be moved between a left lumen position, a right lumen position, and a both lumens position, said control valve comprising:
      (i) a blocker protruding downwardly away from a rotor, said blocker being adapted to rotate radially relative to a barrel;
      (ii) a stop protruding radially inwardly relative to the barrel;
   (b) a connector, said connector being in fluid communication with the control valve;
   (c) a tube, said tube being in fluid communication with the connector and comprising:
      (i) a left lumen, said left lumen being in fluid communication with the connector and having a left lumen proximate end opening and a left lumen distal end opening;
      (ii) a right lumen, said right lumen being in fluid communication with the connector and having a right lumen proximate end opening and a right lumen distal end opening;
   (d) a first cuff, said first cuff being disposed around a portion of the right lumen and the left lumen;
   (e) a second cuff, said second cuff being disposed around a portion of the left lumen; wherein the assembly is adapted to convey airflow or oxygen to a human lung via at least one of the left lumen and the right lumen.

2. The lung isolation tube assembly of claim 1 wherein the control valve comprises an airflow inlet.

3. The lung isolation tube assembly of claim 1 wherein the control valve comprises a left lumen outlet and a right lumen outlet.

4. The lung isolation tube assembly of claim 1 wherein the barrel comprises a detent.

5. The lung isolation tube assembly of claim 1 wherein the control valve comprises an O-ring.

6. The lung isolation tube assembly of claim 1 wherein the rotor comprises a rotor detent.

7. The lung isolation tube assembly of claim 1 wherein the rotor comprises a handle.

8. The lung isolation tube assembly of claim 1 wherein the connector comprises a pair of channels.

9. The lung isolation tube assembly of claim 1 wherein the left lumen distal end opening extends beyond the right lumen distal end opening.

10. The lung isolation tube assembly of claim 1 wherein the left lumen is partially surrounded by the right lumen.

11. The lung isolation tube assembly of claim 1 wherein the left lumen distal end opening is adapted to extend into a human left lung.

12. The lung isolation tube assembly of claim 1 wherein the right lumen distal end opening is adapted to extend to a human right bronchus.

13. The lung isolation tube assembly of claim 1 wherein the second cuff is disposed on the left lumen such that it is positioned in a human left bronchus when the left lumen distal end opening is positioned in a human lung and the right lumen distal end opening is positioned adjacent to a human right bronchus.

14. The lung isolation tube assembly of claim 1 wherein the first cuff is disposed around the right lumen and the left lumen such that it is positioned in a human trachea when the left lumen distal end opening is positioned in a human left lung and the right lumen distal end opening is positioned adjacent to human right bronchus.

15. A lung isolation tube assembly, said lung isolation tube assembly comprising:
   (a) a switch valve, said switch valve being adapted to be moved between a left lumen position, a right lumen position, and a both lumens position and said switch valve comprising:
      (i) a barrel, said barrel having an airflow inlet, a pair of airflow outlets, a detent and a pair of stops that protrude radially inwardly relative to the barrel;
      (ii) an O-ring;
      (iii) a rotor, said rotor having a pair of blockers, a rotor detent, and a handle, wherein the pair of blockers protrude downwardly away from the rotor;
   (b) a connector, said connector being in fluid communication with the switch valve;
   (c) a tube, said tube being in fluid communication with the connector and comprising:
      (i) a left lumen, said left lumen being in fluid communication with the connector and having a left lumen proximate end opening and a left lumen distal end opening;
      (ii) a right lumen, said right lumen being in fluid communication with the connector and having a right lumen proximate end opening and a right lumen distal end opening;
   (d) a first cuff, said first cuff being disposed around a portion of the right lumen and the left lumen;
   (e) a second cuff, said second cuff being disposed around a portion of the left lumen;
   (f) an airflow source; said airflow source being in fluid communication with the switch valve;
   wherein the assembly is adapted to convey airflow or oxygen to a human lung via at least one of the left lumen and the right lumen; and wherein the right lumen partially surrounds the left lumen.

16. A method for isolating a human lung, said method comprising:
   (a) providing a lung isolation tube assembly, said lung isolation tube assembly comprising:
      (1) a control valve, said control valve being adapted to be moved between a left lumen position, a right lumen position, and a both lumens position, said control valve comprising;
         (i) a blocker protruding downwardly away from a rotor, said blocker being adapted to rotate radially relative to a barrel;
         (ii) a stop protruding radially inwardly relative to the barrel;
      (2) a connector, said connector being in fluid communication with the control valve;
      (3) a tube, said tube being in fluid communication with the connector and comprising:
         (i) a left lumen, said left lumen being in fluid communication with the connector and having a left lumen proximate end opening and a left lumen distal end opening;
         (ii) a right lumen, said right lumen being in fluid communication with the connector and having a right lumen proximate end opening and a right lumen distal end opening;
      (4) a first cuff, said first cuff being disposed around a portion of the right lumen and the left lumen;
      (5) a second cuff, said second cuff being disposed around a portion of the left lumen;
   wherein the assembly is adapted to convey airflow or oxygen to a human lung via at least one of the left lumen and the right lumen; and wherein the assembly comprises a single in port and a pair of out ports; and wherein the assembly is adapted to isolate a single lung;
(b) inserting the tube into a human; and,
(c) supplying airflow or oxygen to the lung isolation tube assembly.

* * * * *